United States Patent
Yamada (10) Patent No.: US 7,932,504 B2
(45) Date of Patent: Apr. 26, 2011

(54) MICROSCOPE SYSTEM AND VS IMAGE PRODUCTION AND PROGRAM THEREOF

(75) Inventor: Tatsuki Yamada, Tokyo (JP)

(73) Assignee: Olympus Corporation, Tokyo (JP)

( * ) Notice: Subject to any disclaimer, the term of this patent is extended or adjusted under 35 U.S.C. 154(b) by 157 days.

(21) Appl. No.: 12/343,748

(22) Filed: Dec. 24, 2008

(65) Prior Publication Data
US 2009/0212242 A1    Aug. 27, 2009

(51) Int. Cl.
*G01N 21/64* (2006.01)
(52) U.S. Cl. .................................... 250/461.2
(58) Field of Classification Search ............... 250/461.2
See application file for complete search history.

(56) References Cited

U.S. PATENT DOCUMENTS

| | | | |
|---|---|---|---|
| 6,101,265 A | 8/2000 | Bacus et al. | |
| 6,272,235 B1 | 8/2001 | Bacus et al. | |
| 2003/0210262 A1* | 11/2003 | Gahm et al. | 345/732 |
| 2006/0011861 A1* | 1/2006 | Wolleschensky et al. | 250/459.1 |
| 2007/0069106 A1* | 3/2007 | Krief et al. | 250/201.3 |

FOREIGN PATENT DOCUMENTS

| | | |
|---|---|---|
| JP | 9-281405 | 10/1997 |
| JP | 10-333056 | 12/1998 |
| JP | 2006-343573 | 12/2006 |

* cited by examiner

*Primary Examiner* — Constantine Hannaher (57) ABSTRACT

A whole specimen image generated in the bright view field observation method is displayed, and arbitrary domains are designated. And the fluorescence VS image of each object of interest is generated by acquiring the shape of microscopic image for every small block which is formed by dividing the inside of that object of interest into plurality for every said object of interest, and combining two or more microscopic images generated in the fluorescence observation method. The object of interest is an area where a tumor etc., exist, for example.

1 Claim, 8 Drawing Sheets

MICROSCOPE SYSTEM AND VS IMAGE PRODUCTION AND PROGRAM THEREOF

BACKGROUND OF THE INVENTION

1. Field of the Invention

The present invention relates to a microscope system for generating an image having a wide view field and high resolution, by combining two or more images of microscope.

2. Description of the Related Art

Conventionally, when observing a specimen using a microscope, a view field which can be observed at the same time is mainly determined by a magnification of objective lens. As the observation range becomes smaller, the magnification becomes larger although a high resolution image is obtained. Accordingly, conventionally known system is such that a micrographic image having a wide view field and high resolution is generated by pasting or combining two or more images which were photographed while moving a view field using a motorized stage etc., and then is utilized for a pathology diagnosis etc. (hereafter, this system is called a virtual microscope system.)

For example, in Japanese published unexamined patent application Toku Kai Hei 9-281405 and Japanese published unexamined patent application Toku Kai Hei 10-333056, the virtual microscope system mentioned above has been shown. Namely, in these publications, it has been shown that an image of an observation object is beforehand divided into a small block, and each portion of the observation object corresponding to the small block concerned is photographed by an objective lens of high resolution, and each micrographic image obtained for each small block is pasted or joined together, and then whole image of observation object (micrographic image having a wide view field and high resolution: henceforth called VS (Virtual Slide) image) is reconstructed. The above-mentioned virtual microscope system has been shown. Also, in Publication of the Japanese unexamined patent application, Toku Kai No. 2006-343573, and Toku Hyo No. 2002-514319, as well, a system for making a micrographic image with wide view field and high resolution has been shown.

The VS image having high resolution image of the whole specimen can be seen by anyone, anywhere and anytime as long as personal computer and network environment are available. Therefore, it has become to be utilized for remote consultation among pathology experts in addition to pathology training for medical students, the VS image is also called as Whole Slide Imaging.

For the purpose of complementing the morphological diagnosis based on morphological information on tissue or a cell by using ordinary dyeing such as HE (Hematoxylin Eosin) dyeing and Papanicolaou dyeing which have been used so far, molecular-pathological examination for investigating generation abnormalities of a gene or protein has been carried out. That is, diagnosis of morphological abnormality is performed by the bright field observation by the ordinary dyeing which has been usually used so far, and diagnosis of functional abnormalities such as abnormal generation of a gene/protein has been carried out by a fluorescence observation. Since the fluorescence specimen cannot be preserved for long time, making of VS-image by using a virtual inspection optical system is very useful since it leads also to record and/or storage of the basis of diagnosis.

SUMMARY OF THE INVENTION

The microscope system according to the present invention is characterized in that in a microscope system having a VS image generation means for generating the VS image generated by combining mutually two or more microscopic images obtained by relatively moving an objective lens of a microscope and a specimen along rectangular direction to an optical axis, it comprises: a first VS image generation and/or storage means for storing said VS image which was generated by a first observation method, wherein said VS image of said specimen is generated by said VS image generation means in the first observation method; an object-of-interest designation means, wherein the VS image by the first observation method is displayed, and one or more arbitrary objects of interest are designated on the displayed image, and coordinate information of the object of interest is stored; and a second VS image generation and/or storage means, wherein the VS image of the object of interest is stored by the VS image generation means in a second observation method.

According to the present invention, it is characterized in that the first observation method is a bright field observation method, and the second observation method is a fluorescence observation method.

According to the present invention, it is characterized in that the first VS image generation and/or storage means has an image pick-up coordinate recording section for obtaining a focus map from a focused position in a predetermined focus position extraction point, and then storing it when generating the VS image of the specimen; and the second VS image generation and/or storage means generates the VS image of the object of interest, based on the information on the focus map stored in the image pick-up coordinate recording section when generating the VS image of the object of interest.

According to the present invention, it is characterized in that said microscope system further comprises an image displaying means, wherein the VS image by said second observation method concerning said arbitrary object of interest, and an image of said arbitrary object of interest in the VS image by said first observation method are displayed in parallel or composite form.

According to the present invention, it is characterized in that said microscope system further comprises: a first correction means for correcting coordinates of said object of interest stored by using an amount of deviation of parallel position of the specimen, when the specimen is mounted and demounted in switching to the second observation method, wherein said amount of deviation of parallel position of the specimen is calculated by comparing the image of said specimen generated before mounting or demounting with the image of said specimen generated after mounting or demounting, and coordinates of the object of interest stored are corrected by using said amount of deviation of position; and said second VS image generation and/or storage means generates the VS image by the second observation method by using coordinates of the object of interest corrected.

According to the present invention, it is characterized in that said microscope system further comprises a second correction means, wherein when the specimen used by the second observation method is a sliced piece picked up from neighborhood of the specimen used by said first observation method, an image of the specimen used by the first observation method is compared with an image of the specimen used by the second observation method, and an amount of deviation of the parallel position and rotation between these two specimens are calculated, and coordinates of the observation area are corrected by using the amount of deviation of the parallel position and rotation; and the second VS image generation and/or storage means produce the second VS image by using coordinates of the observation area after the correction.

A method of generating a VS image according to the present invention is characterized in that it is a method of generating a VS image in a microscope system for generating the VS image which is generated by combining mutually two or more microscopic images obtained by relatively moving an objective lens of a microscope and a specimen along rectangular direction to an optical axis, wherein a first VS image generated by generating the VS image of the specimen in the first observation method is stored; the first VS image is displayed, and one or more arbitrary objects of interest are designated on the displayed image, and coordinate information of the object of interest is stored; and then an image of the second object of interest generated by generating the VS image in the object of interest in the second observation method is stored.

According to the present invention, it is characterized in that the first observation method is a bright field observation method, and the second observation method is a fluorescence observation method.

According to the present invention, said VS image generation method is characterized in that when generating the VS image of the specimen in the first observation method, a focus map is obtained from a focused position in a predetermined focus position extraction point, and then stored; and when generating the VS image of the object of interest in the second observation method, based on information on said focus map stored, said VS image of said object of interest is generated.

According to the present invention, said VS image generation method is characterized in that the second VS image concerning the arbitrary object of interest, and an image of the arbitrary objects of interest of the first VS image are displayed in parallel or composite form.

The VS image generation program according to the present invention is characterized in that a computer in a microscope system having a VS image generation means for generating the VS image which is generated by combining mutually two or more microscopic images obtained by relatively moving an objective lens of a microscope and a specimen along rectangular directions to an optical axis is constituted so that it may function as the following means; a first VS image generation and/or storage means for generating the VS image of the specimen by the VS image generation means, and for storing the first VS image generated in a first observation method; an object-of-interest designation means, wherein which the first VS image is displayed, one or more arbitrary objects of interest are designated on the display screen, and then coordinate information of the object of interest is stored; and a second VS image generation and or storage means, wherein the VS image of the object of interest is generated by the VS image generation means in the second observation method, and the second VS image generated is stored.

According to the present invention, the VS image generation program is characterized in that the first observation method is a bright field observation method, and the second observation method is a fluorescence observation method.

The VS image generation program according to the present invention is characterized in that when said first VS image generation and/or storage means generates said VS image of said specimen, said computer executes so that a focus map may be obtained from a focused position in a predetermined focus position extraction point, and the photographic coordinate recording section may function to store the focus map; and when said first VS image generation and/or storage means generates said VS image of the object of interest, said computer executes so that said VS image of said object of interest may be generated, based on the information of said focus map stored in said photographic coordinate recording section.

According to the microscope system, its VS image generation method, program, and the like of the present invention, by designating a portion of the area of the specimen on the whole image of the specimen generated in the bright field observation method, and generating the VS image to this portion of the area (tumor site etc.) in a fluorescence observation method, a process time for generating a fluorescence VS image which is a VS image generated in the fluorescence observation method can be shortened very much, and the data size of the fluorescence VS image concerned can be reduced.

These and other features and advantages of the present invention will become apparent from the following description of the preferred embodiments when taken in conjunction with the accompanying drawings.

DETAILED DESCRIPTION OF THE PREFERRED EMBODIMENTS

Hereafter, with reference to drawings, embodiments of the present invention will be explained.

Figure 1:
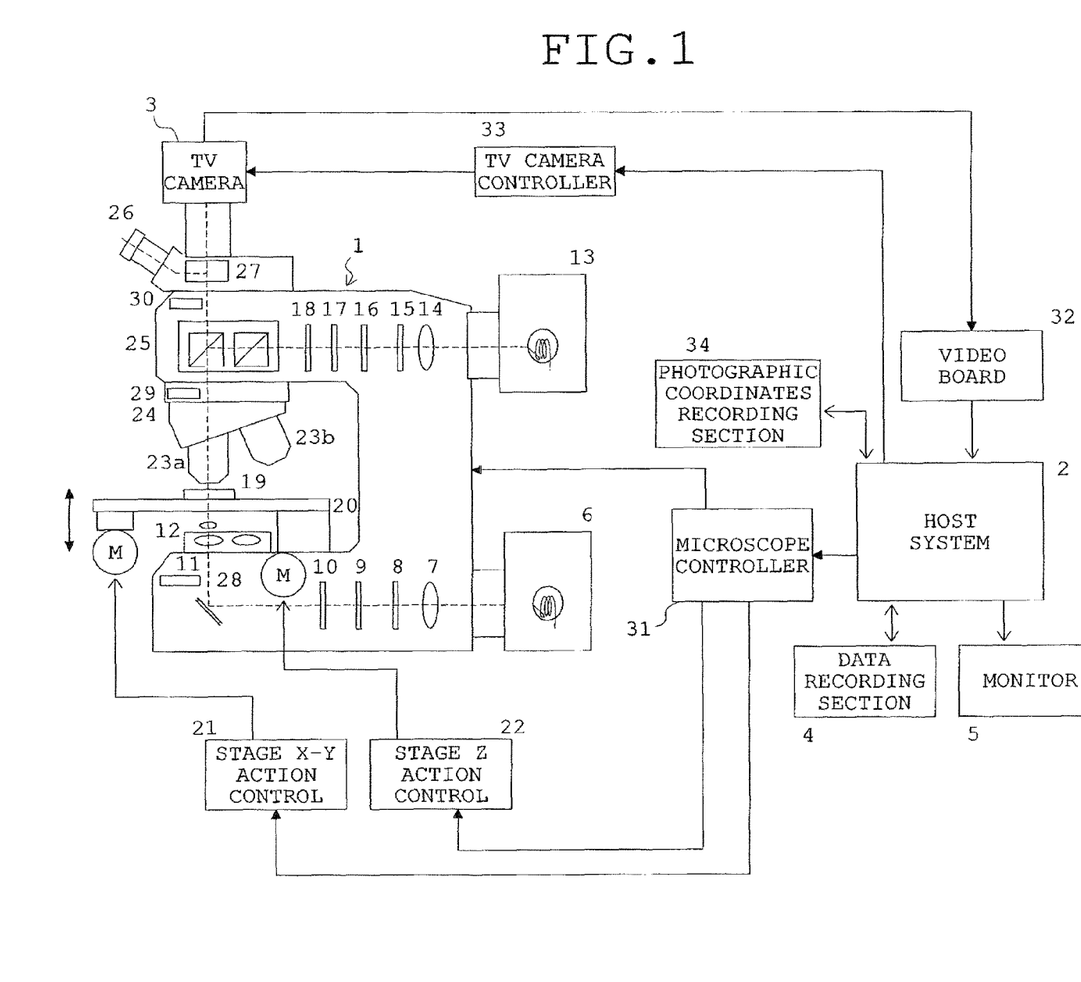
FIG. 1 is a diagram showing an example of whole constitution of the microscope system according to the present invention.

FIG. 1 shows an example of whole constitution of the microscope system according to the present invention. The microscope apparatus 1 shown in FIG. 1 has as an optical system for transmitting light observation, a light source 6 for transmitting light illumination; a collector lens 7 for collecting illumination light of the light source 6; a filter unit 8 for transmitting light; a field stop 9 for transmitting light; an aperture stop 10 for transmitting light; a condenser optical element unit 11; and a top lens unit 12. Furthermore, it has as an optical system for vertical light observation; a light source 13 for vertical light illumination; a collector lens 14; a vertical illumination filter unit 15, a vertical illumination shutter 16; a vertical illumination field stop 17; and a vertical illumination aperture stop 18.

Furthermore, a motorized stage 20 for mounting the specimen, which can move toward directions parallel to and perpendicular to the optical axis, is arranged on an observation optical path where an optical path of transmitting light observation optical system and an optical path of a vertical light observation optical system overlap. Movement control of the stage 20 is carried out with a stage X-Y drive control part 21 and a stage Z drive control part 22. The stage 20 has a zero position detecting function (not illustrated) by a zero sensor, and a coordinate can be set up to each part of specimen 19 mounted on the stage 20.

On the observation optical path, a revolver 24 for selecting one of the objective lens 23 to be used for observation by rotation operation out of two or more objective lenses 23a and 23b - - -, which were mounted (hereafter called generically "the objective lens 23" if necessary); optical cubes 25a and 14b which are selectively inserted in the optical path according to mirror inspection method (hereafter, generically called "the optical cube 25" if necessary); a beam splitter 27 for dividing the observation optical path into the side of eyepiece 26 and the side of TV-camera 3 are arranged. Further, a polarizer 28 for differential interference observation, DIC (Differential Interference Contrast) prism 29 and an analyzer 30 can be inserted into the observation optical path. Furthermore, each of units is motorized type namely electrically driven type, and the operation is controlled by a microscope controller 31 mentioned later.

The microscope controller 31 connected to the host system 2 has a function for controlling operation of whole microscope-apparatus 1 and further has functions as follows; namely, function for controlling each of the units, such as change of a mirror inspection method, for controlling the light source 6 for transmitted light illumination, and the light source 13 for vertical-illumination etc., according to a control signal from the host system 2, and, at the same time, for sending a signal detected to the host system 2 by detecting a current state of each unit by a current microscope apparatus 1.

Furthermore, the microscope controller 31 is connected also to the stage X-Y drive control part 21 and the stage Z drive control part 22, wherein the host system 2 can also perform control of the motorized stage 20 through the microscope controller 31.

A microscope image of the specimen 19 (observation object) imaged by CCD which is an imaging element in TV camera 3 is taken into the host system 2 through a video board 32. The host system 2 can carry out through the camera controller 33 to TV camera 3, ON/OFF of automatic gain control, setup of gain, ON/OFF of automatic exposure control, and setup of exposure time. Moreover, the host system 2 can store the microscope image sent from TV camera 3 as an image data file in the data recording section 4. The data recording section 4 is a hard disk, a large capacity memory, etc., for example. As for image data recorded on the data logging part 4, by a user's operation at any time when the user desires, it is read by the host system 2 and can be displayed on a monitor 5 that is a display part.

Further, the host system 2 has a function so called a video AF function for performing focusing operation based on the contrast of an image picked up by the TV camera 3, and also a function for recording coordinates of the focus position obtained by the video AF function on an image pick-up coordinate recording section 34. The host system 2 is a computer of standard constitution. It has CPU (central process unit) for managing operation control of the whole microscope system by execution of control program; a main memory which the CPU uses as a work memory if needed; an input part for acquiring various kinds of orders from users via a mouse, a keyboard, etc.; an interface unit for managing transfer of various data between each of compositions mentioned above of the microscope system; and an auxiliary memory for storing various kinds of programs and data, such as a hard disk drive unit, for example; and a display apparatus for displaying data or information (not illustrated).

When the CPU reads a predetermined application program stored by the auxiliary memory on a main memory, and executes it, various kinds of processes (in particular, processes according to flow charts shown in FIGS. 2, 8, and 10, and processes explained by FIGS. 7 and 9 etc.) mentioned later are executed. In these processes, there is a case that the host system 2 transmits a control signal to the microscope controller 31, and movement control of the stage 20 mentioned above for example, and detection of a state of each unit of the microscope apparatus 1 in change of a mirror inspection method, etc., are carried out by the microscope controller 31. However, such processes as mentioned above will not be explained in detail in the following explanation.

Hereafter, operation of the microscope system shown in FIG. 1 will be explained.

In this embodiment, a case that the bright field observation is selected as the first observation method, and fluorescence is selected as the second observation method will be explained.

Figure 2:
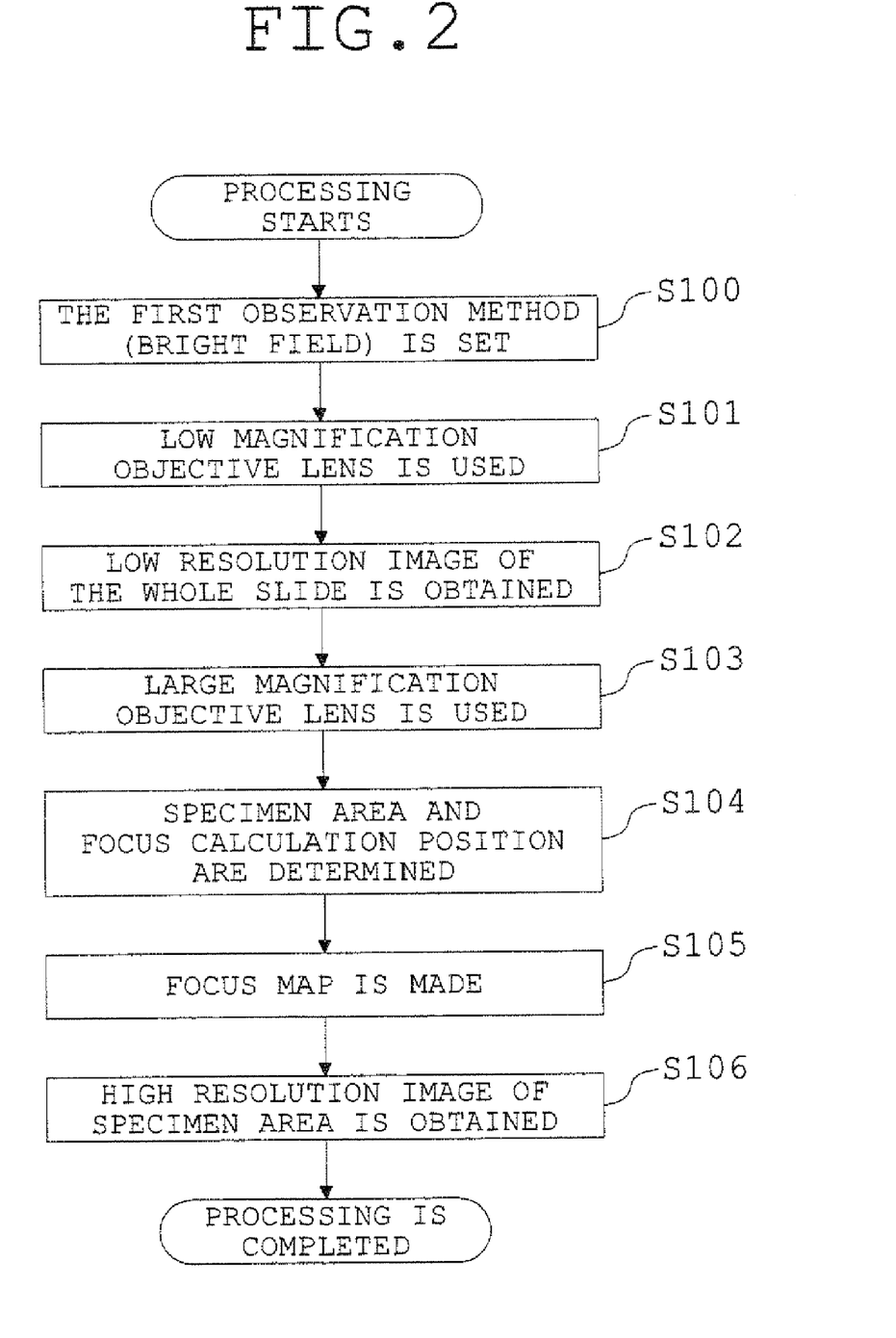
FIG. 2 is a flow chart showing a VS-image generating process by a first observation method (bright field observation).
Figure 3:
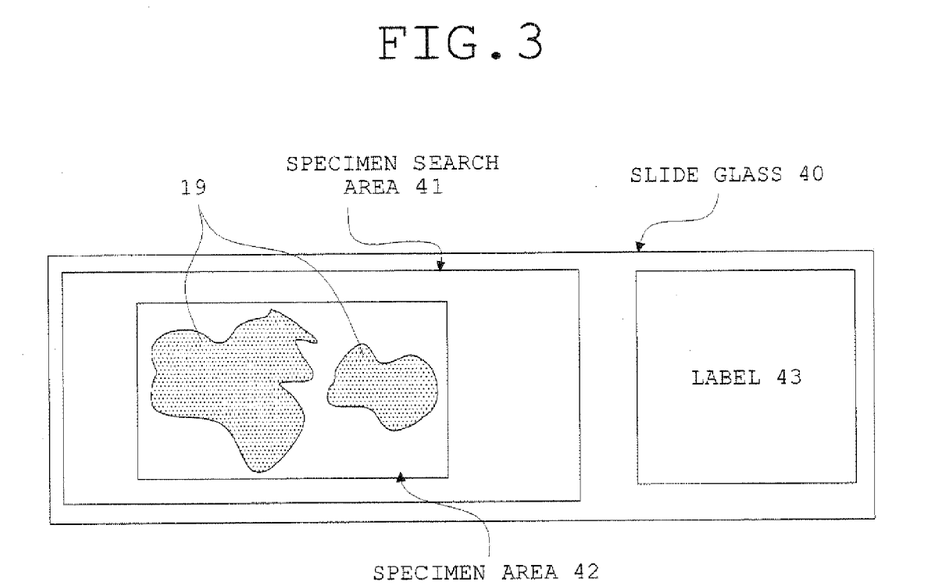
FIG. 3 is a diagram showing an example of a slide glass specimen.
Figure 4:
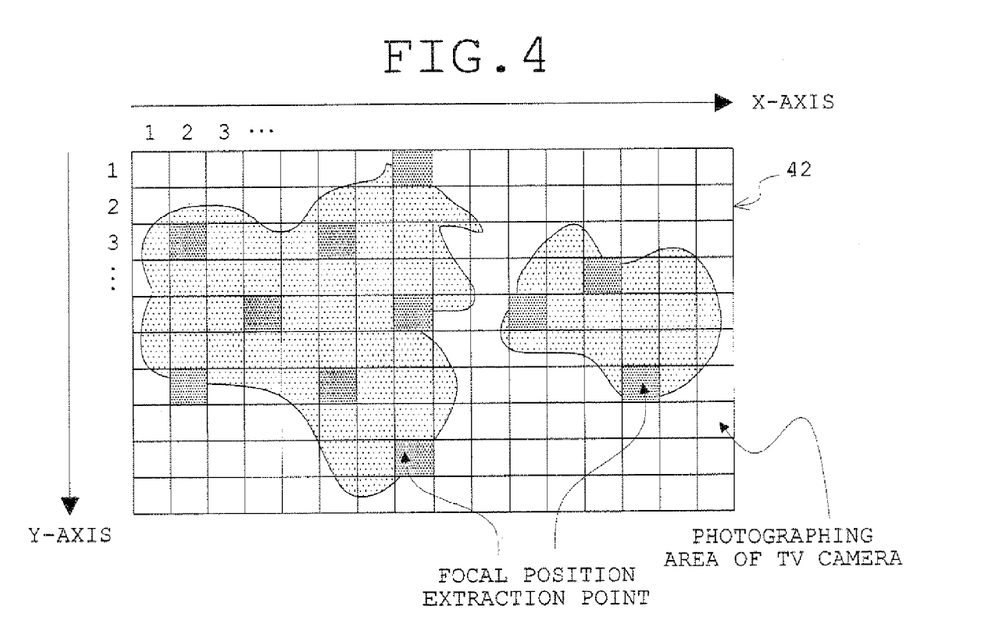
FIG. 4 is a diagram showing a state where the image of the whole specimen area is divided into many small blocks for making a focus map.
Figure 5:
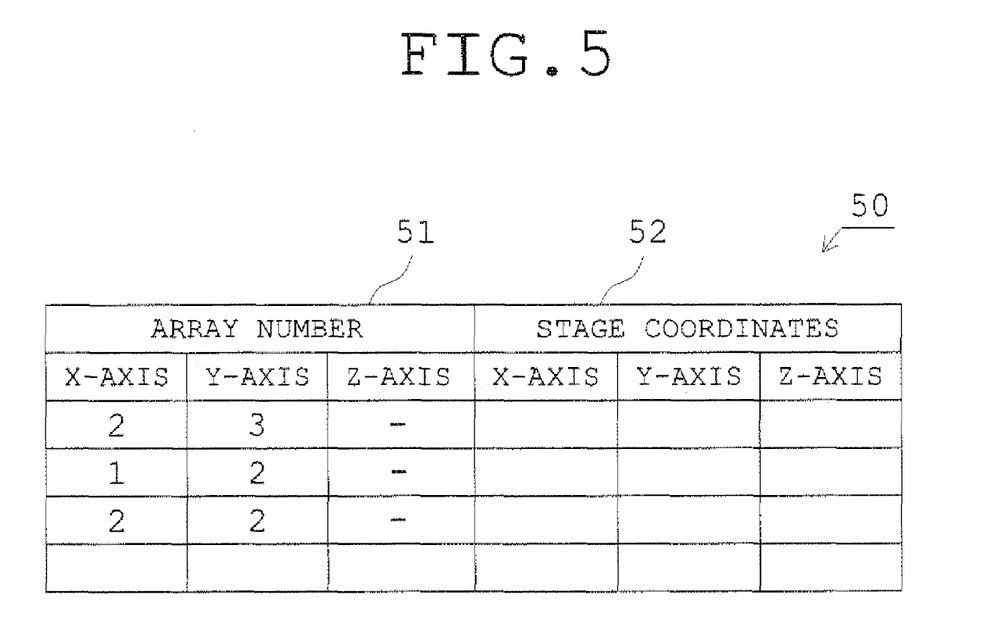
FIG. 5 shows an example of data configuration of the focus map.

FIG. 2 is a flow chart showing a VS-image generating process by the first observation method (bright field observation). Here, image in a broad sense, VS image is an image which is generated by combining two or more pieces of micrographic. In a narrow sense, it is a micrographic image having a wide view field and high resolution, which is generated by combining two or more pieces of micrographic image as mentioned above, particularly. FIG. 3 is a diagram showing an example of a slide glass specimen (the specimen 19 is placed on a slide glass). In FIG. 1, only the specimen 19 is shown. However, in actual case, a slide glass specimen is set on the motorized stage 20. Therefore, hereafter, there is a case that it is described as the slide glass specimen 19. FIG. 4 is a diagram showing a state where the image of the whole specimen area is divided into many small blocks for making a focus map. FIG. 5 shows an example of data configuration of the focus map.

Hereafter, referring to FIGS. 3-5, VS-image generating process by the first observation method (bright field observation) shown in FIG. 2 will be explained. However, as for this process, it has been shown in Japanese published unexamined patent application, Toku Kai 2006-343573 which was filed by the present applicant, and detail explanation has been described in Japanese published unexamined patent application Toku Kai Hei 9-281405 which was filed by the present applicant. Accordingly, explanation will be made briefly. Here, the process shown in FIG. 2 is carried out by the host system 2 as mentioned above.

First, in the step S100 in FIG. 2, a control for inserting into and pulling from the optical path of various light elements is done in order to carry out the transmitting light bright field observation method. Namely, in order to set a transmitting light bright field observation state, a vertical light shutter 16 is inserted into an optical path by the microscope controller 31, and an optical cube 25 for bright field observation is inserted into the optical path, and thus control for turning on the light source 6 for transmitting light illumination 6 is carried out. That is, control for switching an observation method to the bright field observation method is done. Then, processes of the following steps S101-S106 are carried out in the bright field observational method.

First, in the step S101, objective lens 23 having low magnification of four for example, is inserted into the optical path.

Next, in the step S102, a predetermined specimen search area 41 (for example, 25 mm long and 50 mm wide) on the slide glass 40 shown in FIG. 3 is divided according to the width of a projection area which is to be projected on TV camera 3 (namely, it is divided according to the magnification of the objective lens 23 inserted in the optical path at the step S101). Then, to each of two or more blocks which are formed by dividing the specimen search area 41 concerned, the motorized stage 20 is moved to XY directions, and a micrographic image through the TV camera 3 in the block where the motorized stage 20 is located is repeatedly acquired. The image (an image of whole specimen search area 41 shown in FIG. 3) of the whole of the slide is generated by combining mutually two or more micrographic images obtained by the steps (images of each block by low magnification), and it is stored as a whole slide image file to the data recording section 4. Here, movement of the XY directions mentioned above means by movement of rectangular directions to the optical axis on a plane, and indicates that control of movement of the motorized stage 20 is carried out by the stage X-Y drive control part 21. The specimen search area 41 is an arbitrary area set beforehand on the slide glass 40, and the specimen 19 is certainly mounted within the specimen search area 41. As shown in FIG. 3, on the slide glass 40, an area in which a label 43 is pasted is determined beforehand.

Next, in the step S103, objective lens 23 having large magnification (40 times, for example) which is determined beforehand (or designated by operation of an operator, etc.) is inserted into the optical path. This step is to change the objective lens 23, in order to acquire a high resolution image in the first observation method (bright field observational method). Then, in the step S104, on a basis of whole image of the specimen search area 41 acquired by the step S102, an area where the specimen 19 is actually placed on the slide glass 40 is extracted automatically (the specimen area 42 shown in FIG. 3 is determined). As for the process for determining of the specimen area 42, explanation of it will not be made in detail in particular since it can be carried out by a conventional method. For example, the specimen area 42 is determined to be formed rectangle, beforehand, and the specimen area 42 can be determined by searching a portion where the specimen is placed, along the direction of X and the direction of Y, wherein binary formatting is carried out to the whole images according to existence or non-existence of the specimen. Here, the operator etc., may operate a mouse and designates the specimen area 42 arbitrarily.

Then, this specimen area 42 is divided into grids (hound's-tooth check) for example, as shown in FIG. 4. The size of area of one block (small block) of this hound's-tooth check expresses a photographing area to be projected on the TV camera 3 when a large magnification objective lens 23 selected by the step S103 mentioned above is used. The XY coordinates on a diagram screen in FIG. 4 of each small block (here, each small block is a rectangle, for example, center coordinates of rectangular shape) are obtained. Then, the coordinates on this diagram are converted into the XY coordinates on the motorized stage 20. As for the calculation method of converting the XY coordinates on the image into the physical XY coordinate on the actual motorized stage 20, it is computed from photographing magnification or imaging element information (a pixel number or pixel size), and since it is described in detail in Japanese published unexamined patent application Toku Kai Hei 9-281405, its explanation is omitted.

Then, a focused position (Z coordinate) for every small block of this hound's-tooth check is obtained. However, For example, when the number of blocks is large as shown in FIG. 4, time will be taken very much if obtaining the focused position by actual measurement about all the small blocks. Accordingly, in the present example, the small block (for example, focus position extraction point shown in FIG. 4) of which sampling (actual measurement) is made out of all the small blocks is extracted automatically. This automatic extraction may be extracted at random for example, and may be extracted regularly (for example, by every three blocks). That is to say, the content of automatic extraction process can be determined arbitrarily.

Then, in the step S105, the motorized stage 20 is moved to the XY directions; an optical axis position is moved to each focus position extraction point extracted at the step S104; and while carrying out its movement to Z axial direction for every extraction point, a specimen image is inputted and contrast is evaluated through the TV camera 3. Thus, the focused position (Z coordinate) is obtained by actual measurement. Furthermore, as for an area (small block) which was not extracted as a focus position extraction point by the step S104, a focused position (Z coordinate) is obtained by interpolation operation based on the actually measured focused position (Z coordinate) of the focus position extraction point at the neighborhood of the small block.

By carrying out the processes mentioned above, for example, a focus map 50 shown as an example in FIG. 5 is generated, and this is stored in the photographic coordinate recording section 34. In the focus map 50 illustrated, array number 51 of the small block and stage coordinate 52 are stored for every each small block which was used for obtaining the focused position (Z coordinate). The array number 51 is a number regularly assigned to each small block, as shown, for example in FIG. 4 (for example, 1,2,3 - - - are assigned to each of small blocks in X and Y directions). For example, the array number 51 of the small block of the upper left end of the specimen area 42 of diagram is (X axis, Y axis)=(1, 1). In an example shown in FIG. 5, the array number 51 has Z axis. This is necessary when generating "VS fluorescence image of the three dimensions which have different focus positions" mentioned later. Therefore, here, it will be explained as a necessary matter especially. A stage coordinate 52 is a center coordinate of its small block. The X axis-Y coordinates in this stage coordinate 52 are not the coordinates on the image shown in FIG. 4, but physical XY coordinates on the motorized stage 20.

Then, in the step S106, the motorized stage 20 is controlled based on the information on the focus map 50 generated mentioned above, and an image for every small block is obtained. That is, an optical axis position and a focused position are moved to the XYZ coordinates which are indicated by each stage coordinates 52 registered in the focus map 50, and the image is inputted through the TV camera 3. Then, the image of each inputted small block is combined with an image of the small block adjoining the image each other. Such image inputting and combining processes are repeatedly carried out until these processes are completed to all the small blocks registered into the focus map 50. By such processes, the image of whole specimen area 42 which is combined mutually with micrographic images having high resolution using an objective lens 23 having large magnification, namely, micrographic image (VS image) having a wide view field and a high resolution is completed, and it is stored as a whole slide image file in the data recording section 4.

The process from steps S101 to S106 is automated. By operator's action only for putting the slide glass specimen 19 on the motorized stage 20, and carrying out a start operation for scanning of a scanning screen which is not illustrated, high resolution micrographic image having wide view field can be generated automatically. An image file stored in the data recording section 4 can be stored in a compressed form by compression algorithm such as well known JPEG and JPEG2000. Here, it should be noted that there is no distinct demarcation between "low magnification" and "large magnification" concerning the objective lens 23. In examples mentioned above, twice, four times, and the like are treated as "low magnification", and 40 times, 60 times, etc., are treated as "large magnification". But, these are not restricted by these examples. However, as a matter of course, an objective lens 23 of "large magnification" has a larger magnification than that of the objective lens 23 of "low magnification". As for "low magnification" and "large magnification" mentioned above, it is necessary to satisfy a condition such as relative meanings between "low magnification" and "large magnification" mentioned above. As a matter of course, it is possible to read a slide specimen number printed as a bar code on the label 43, etc., of the slide glass specimen 19 by using a barcode reader (not illustrated) connected to the host system 2, and at the same time to record it as a supplementary information of the image file stored in the data recording section 4.

As a matter of course, adjustment in each of the following steps is possible. Namely, it is possible to stop once at any desired steps in S101~S106; to be operated by an operator; to change of a specimen area; to change/add/delete of the focus position extraction point for sampling; and to change a magnification of the large magnification objective lens 23 to be used. Furthermore, it is also matter of course that the illumination system of a microscope is optimized when the objective lens 23 is changed.

As shown in Japanese published unexamined patent application Toku Kai Hei 9-281405, it is also possible to overcome discontinuity of images accompanied by stage accuracy by using processes such that it is moved on each of small blocks by setting an image overlap area of the small blocks adjoined; each image including the overlap area is acquired; and a process for combining of each of these images is carried out, when the motorized stage 20 is moved along XY directions (horizontal movement; movement intersecting perpendicularly to the optical axis on a plane). In that case, the area size of one block of the focus map formed by the step S105 is a size that excludes an overlap area for combining process from the photographing area projected on the TV camera 3 when using the large magnification objective lens 23.

In FIG. 6, an example of a format of VS-image data stored as an image file to the data recording section 4 (an example of data configuration) is shown. VS image file 60 shown in the diagram consists of supplementary information 61, specimen search area image data 62, high resolution image data having wide view field 63, and object-of-interest designation information 64. Supplementary information 61, as shown in FIG. 3, consists of information of the observation method 71 and the photographing magnification 73 of the specimen search area image data 62, etc. The observation method 71 is an observation method used when the high resolution image data 63 having wide view field was generated, and it is the bright view field observation method, the fluorescence observation method, etc. Slide number 72 is an identification number which is arbitrarily assigned to each slide glass specimen 19, and for example, its bar code is printed on label 43 as mentioned above, and it is inputted.

Figures 6A, 6B, 6C, 6D:
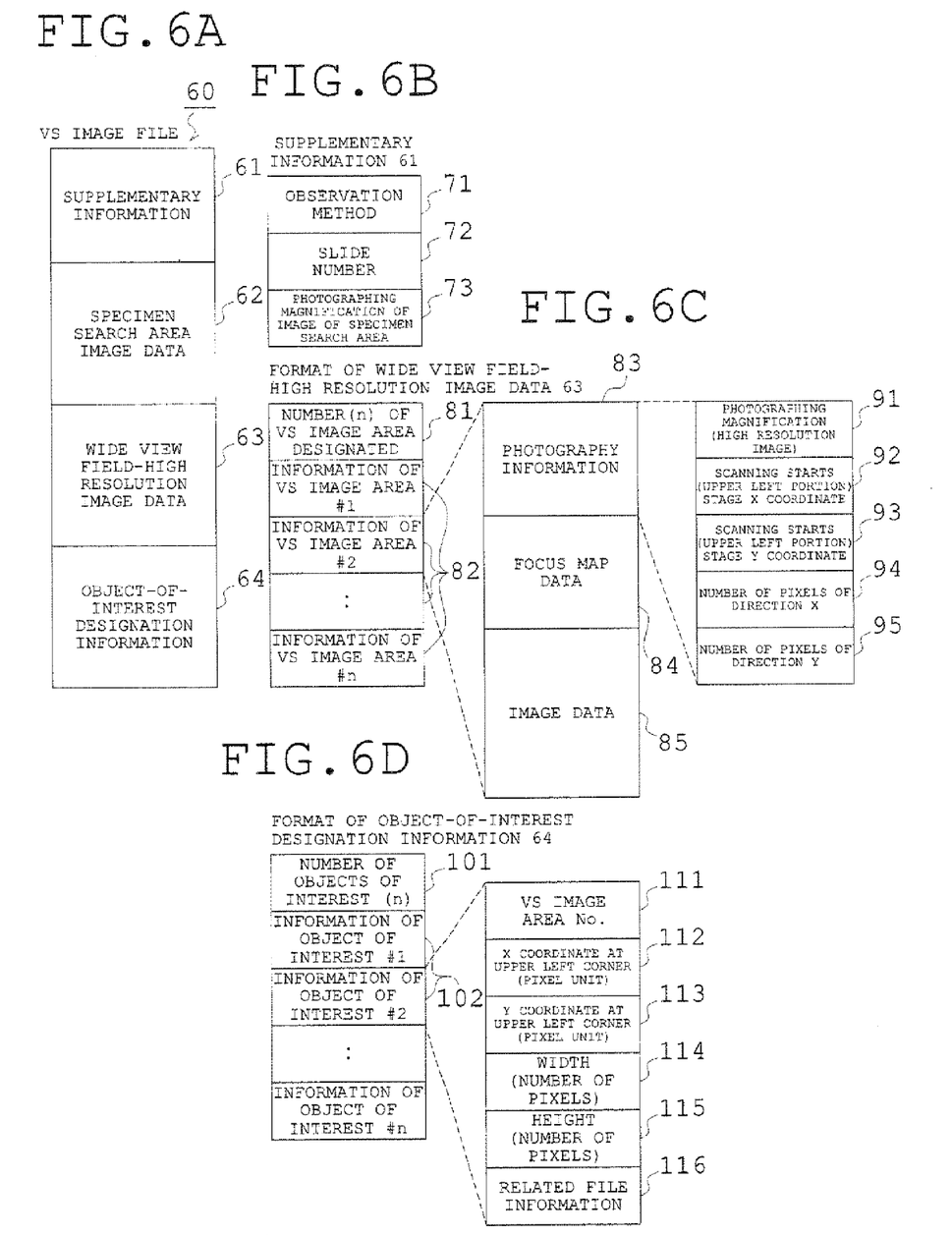
FIGS. 6A, 6B, 6C, and 6D are diagrams showing examples of composition of a VS image file, wherein an example of the whole constitution, and an example of a constitution of each of different parts are shown, respectively.

The specimen search area image data 62 is an image with low resolution of the whole specimen search area 41 obtained by process of the step S102 (obtained by combining images by using low magnification objective lens 23). "Photographing magnification of specimen search area image data 62" 73 is a magnification of the objective lens 23 (low magnification) when the specimen search area image data 62 is generated. A high resolution image data having wide view field data 63 is hidden information concerning this VS image and a VS image (high resolution micrographic image having wide view field) generated by process of steps S115, and S207. The data constitution is shown in FIG. 6C. This VS image is a bright field VS image in the step S106, but it is a fluorescence VS image in the steps S155 and S207 mentioned later.

In an example shown in FIG. 6C, where a case that two or more VS images are stored in one of the VS image file 60 is also supposed, each VS image area information 82 (information of VS image area #1, information of VS image area #2, - - - information of VS image area #n) is stored. And, the number of these VS image area information 82 (in the example of illustration, the number is n that is from #1 - - - #n) is stored in VS image area designation number 81. However, when the VS image concerned is a bright field VS image generated by the step S106 mentioned above, only one image is generated as mentioned above. Accordingly, in this case, VS image area information 82 is always '1' (namely, only the information of VS image area #1 is stored). As shown in FIG. 6C, each VS image area information 82 consists of photography information 83, focus map data 84, and image data 85, respectively.

Photography information 82 consists of data of photography magnification 91, scanning start (upper left block) stage X coordinate 92, scanning start (upper left block) stage Y coordinate 93, the number of pixel 94 in the direction X, and the number of the pixel 95 in the direction Y, as illustrated for example. The photography magnification 91 is a magnification of the objective lens 23 at the time of photographing of the image data 85. Other data (92~95) are data showing a position coordinate (coordinate on the motorized stage) of the image data 85 and its size. The focus map data 84 is a focus map 50 generated by process of the step S105, or the step S153 or S205 mentioned later (an example is shown in FIG. 5). The image data 85 is data of VS-image (bright field VS image or fluorescence VS image) generated by process of the steps S155 and S207.

Since object-of-interest designation information 64 has not been yet generated in the process in the FIG. 2, it will be explained later. Fundamentally, the object-of-interest designation information 64 is stored, basically when it is a bright field VS image file of the VS image file 60 concerned. However, it is not restricted within this example. For example, by displaying arbitrary fluorescence VS image in order to designate arbitrary object of interest on this image, it is possible to produce further a fluorescence VS image about this object of interest. In this case, the object-of-interest designation information 64 is stored also when it is a fluorescence VS image file of the VS image file 60 concerned.

Figure 7:
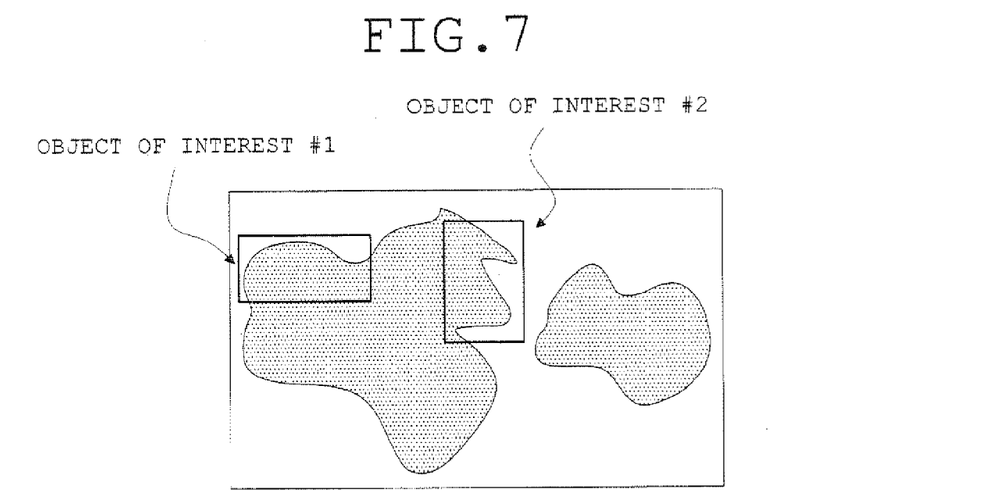
FIG. 7 is a diagram showing an example by which an arbitrary object of interest is designated by displaying bright field VS image.

Next, an example of operation for setting a fluorescence photography area of a tumor part and the like by using the bright field image generated by the process in FIG. 2 mentioned above will be explained by FIG. 7. FIG. 7 shows a state where the whole image is displayed on the monitor 5 by reducing the size of the bright field image mentioned above. On this screen, for example, specialist (medical doctor, etc.) sets an area (objects of interest #1, #2 etc., as shown in the diagram) in which a fluorescence VS image is obtained by operation of a mouse (not illustrated) like a general designation method of a square area (for example, by designating an upper left corner→a lower right corner).

Then, by storing operation (not illustrated), these contents which were set are stored in the object-of-interest designation information 64 of the bright field VS image file used for display in FIG. 7. That is, as shown in FIG. 6D, the objectof-interest designation information 64 consists of the number 101 of objects of interest, and the object-of-interest information 102. In an example shown in FIG. 7, the number of the objects of interest 101 becomes 2 (101='2'), and by each of objects of interest #1, #2 which were designated as mentioned above the information of object of interest #1 and the information of object of interest #2 are stored.

Each object-of-interest information 102 consists of VS image area 111, upper left corner X coordinate (pixel unit) 112, upper left corner Y coordinate (pixel unit) 113, width (the number of pixel) 114, height (pixel unit) 115, and related file information 116, respectively. The VS image area 111 is for an identification number arbitrarily assigned to each of the objects of interest mentioned above. As for upper left corner X coordinate (pixel unit) 112 to height (pixel unit) 115, these are information showing the position and the size of the object of interest on the image shown in FIG. 7. Not only this example, further the XY coordinates of a lower right corner may be stored for example. Namely, any two arbitrary tops which are faced, out of four tops of the object of interest (rectangle), or arbitrary XY coordinates of the tops which are faced may be stored. In the related file information 116 which is one item of the object-of-interest designation information 64, a name of the VS-image-file generated by the second observation method (fluorescence) which will be mentioned later is stored (therefore, at this stage, the information has not yet been stored).

Figure 8:
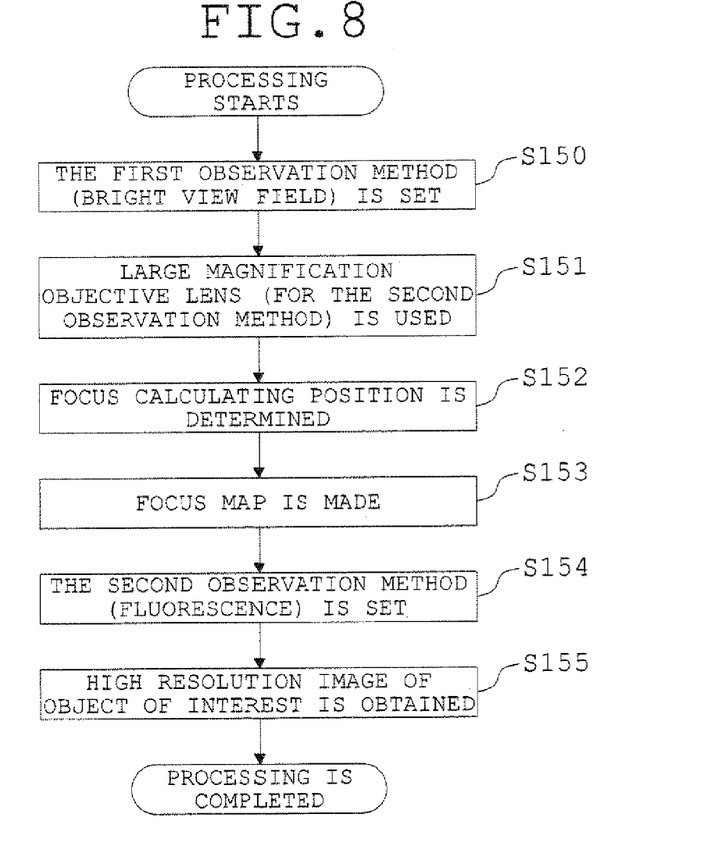
FIG. 8 is a flow chart showing a generating process of the VS image in the object of interest.

Next, as for each of objects of interest set up by designating the objects of interest, flow of process for generating a high resolution micrographic image having wide view field (VS image) by using the second observation method (fluorescence) will be explained with reference to FIG. 8. FIG. 8 is a flow chart showing a generation process of a fluorescence VS-image in the object of interest designated as mentioned above. Here, as for the same contents of process as the VS-image process by the bright field explained by the FIG. 2 etc., it will be explained simply. In process shown in FIG. 8, it is premised that as for the specimen used by process of FIG. 2, specimen for which dyeing for morphology observation was carried out and fluorescence sign for detecting molecular information was given simultaneously is used. Therefore, it is assumed that there is no mounting and demounting of the specimen, and there is no deviation of the stage position. The process in FIG. 8 starts when the arbitrary bright field VS image files where one or more objects of interest are designated, and instructions for "produce fluorescence VS-image" (not illustrated) is issued.

First, in the process of step S150 shown in FIG. 8, controlling for inserting various optical components into an optical path and pulling them out is carried out in order to achieve the transmitting light bright-field observation method. Next, in the process of step S151, for example, an objective lens 23 having magnification of 60 times or the like, (predetermined or designated arbitrarily by the operator etc.) is inserted into the optical path. That is, it is to switch to the objective lens 23 for obtaining a high resolution image in the second observation method. As mentioned above, since there is a case such that fluorescence VS image may be generated by using a different objective lens 23 from that having large magnification as many objective lens (40 times in the example mentioned above) used in the process of FIG. 2, it is necessary to make a focus map again as follows.

Then, a focus position is computed like in the process of the step S104 (step S152), and a focus map is generated like in the process of the step S105 (step S153). These processes are carried out respectively, for every each of the object of interest which was set by the object-of-interest designation means. As mentioned above, the information on each object of interest is stored in the object-of-interest designation information 64 on the bright-field VS graphics file designated in the start of the process mentioned above. Of course, a focus map to be generated becomes a map corresponding to the objective lens 23 which has magnification of 60 times.

Then, in step S154, as for various optical components, control for inserting them into the optical path and pulling them out is carried out in order to achieve a vertical light fluorescence observation method. That is, through the microscope controller 31, the light source 6 for transmitting light illumination is switched off, and the optical cube 26 for fluorescence observations is inserted into the optical path, and then control for opening the vertical shutter 16 is carried out. Then, the process in the same way to the step S106 is carried out for every each of the object of interest, respectively (step S155). Namely, the image of each small area is photographed for every object of interest based on the information on the focus map 50 generated in the step S153. That is, by controlling for moving the motorized stage 200 toward each of designated XYZ coordinates (stage coordinates 52) registered in the focus map 50, an image of the small block is inputted through the TV camera 3 at each place where it was moved. Then, as for the inputted image, process for combining the inputted image with this adjoined image is carried out, when there is an image of the small block which adjoins the small block of the current position in the images which were inputted before.

By carrying out repeatedly such processes, consequently, a VS image of an object of interest namely, an image having a large view field and high resolution of the whole object of interest is generated (however, an image by the second observing method, namely, a fluorescence VS image). The generated fluorescence VS image is stored in the data recording section 4 as an image file. Furthermore, a name of such fluorescence VS image file is recorded in the related file information 116 in a corresponding bright field VS image file (designated when the process in FIG. 8 starts). When there are other objects of interest, a fluorescence VS image of the object of interest is generated similarly, and it is stored in the data recording section 4 as an image file, and then, a name of the file name is recorded on the related file information 116. When the fluorescence VS image of all of the objects of interest set as mentioned above is generated, this process is completed. In the process mentioned above, a fluorescence marker specimen is used from the beginning as mentioned above in order to prevent from fading of a specimen and to improve process speed, the focus position etc., is obtained in the bright-field observation. However, it is not restricted by only such example as mentioned above. A focus position, etc., may be determined in the fluorescence observation.

In order to produce a three-dimensional fluorescence VS image having a different focus position, the image can be also generated as follows. That is, a predetermined distance determined with a depth of focus of the objective lens inserted into the optical path is set as a basic unit, and Z coordinate (focus position) registered in the focus map is used as a center, and controlling for moving the motorized stage 20 up and down (toward Z shaft orientations) is carried out twice or more times, and two or more fluorescence images by a different Z coordinate in same XY coordinates may be photographed. As for the detail, it has been described in Publication of the Japanese unexamined patent application, Toku Kai 9-281405 etc., further explanation is omitted.

In order to prevent unnecessary excitation of a specimen when the motarizedic stage 20 is moved toward the XY directions, it is also possible to carry out control for opening and closing the vertical light shutter 16. Furthermore, as a matter of course, in order to excite only the area to which light is projected on an imaging element of TV camera 3 through the objective lens 23, the vertical light field diaphragm 17 is adjusted to the necessary minimum range.

With respect to a background part in which a specimen does not exist on a bright field image, a fluorescence image is not photographed actually, and no data is substituted for it. Further, naturally, it is possible to avoid including an unnecessary area by constituting so that setting of an area of tumor part etc., mentioned above may be carried out by a multipoint designation or free line designation instead of designation of rectangle.

Since according to the embodiment described above (the first embodiment), the area of a tumor site can be easily designated on a bright field image (two or more designations are possible) and the automatic generation of the fluorescence VS image of this observation area can be carried out, generation of the fluorescence VS image to the necessary minimum area excluding a non-tumor part, a background part, etc., is possible, and accordingly shortening of VS-image generation time and reducing of VS-image capacity can be realized.

Hereafter, referring to FIGS. 7 and 9, a process for correcting a fluorescence VS image whenever it is needed, by displaying two kinds of VS image files (a bright field and fluorescence) generated as mentioned above, in parallel or overlapped state will be explained. Namely, here, the explanation will be made on the assumption that a state where the bright field VS image file and the fluorescence VS image file are stored in the data recording section 4 by the various processes mentioned above. In this case, as mentioned above, it is a state where information of each of objects of interest and its fluorescence VS image file are generated to be related with a bright field image by the designated information 64 of the object of interest in the bright field VS image file.

As for processes which will be explained hereafter, it is executed by the host system 2 as already stated. That is, as mentioned above, this process is realized by a process such that CPU (not illustrated) in the host system 2 reads a predetermined application program stored in a storage apparatus (hard disk etc., not illustrated), and executes it. Here, it is assumed that images of FIG. 7 and FIG. 9 shall be displayed on a monitor together. And, it is assumed that in the initial state, nothing is displayed in an area of FIG. 7. Similarly, nothing is displayed in a left side window 120 shown in the lower left of FIG. 9, and nothing is displayed in the right side window 121 shown in the lower right of FIG. 9. On the other hand, it is assumed that a display magnification selecting button 122 shown in FIG. 9, a scroll button 123 for scrolling vertically and horizontally, and "parallel/overlap" button 124 are displayed from the initial state.

First, when a user etc., operates a keyboard or a mouse, and opens a desired bright field VS image file, a screen shown in FIG. 7 is displayed on the monitor 5. The screen shown in FIG. 7 displays the whole bright field image by reducing the image as already explained. However, here, since the object of interest was already set, the objects of interest #1 and #2 as illustrated are displayed by carrying out read-out the object-of-interest designated information 64. In this case, in order to make it intelligible, the objects of interest #1 and #2 are displayed by using specific colors. Then, when the user operates the mouse etc., and sets a cursor with a desired object of interest (in this example, either of objects of interest #1 and #2), and then starts operation of a synchronous display of the fluorescence VS image (not illustrated), an portion of the object of interest designated as mentioned above is picked up from the bright field image currently displayed as mentioned above, and this portion (a part of bright field image) is displayed on the left side window 120. At the same time, by referring to the related file information 116 in the object-of-interest designated information 64 in the bright field VS image file opened as mentioned above, a fluorescence VS image file of the designated object of interest concerned is opened, and it is displayed on the right side window 121.

In this state, when the user (operator etc.) choose an arbitrary magnification on the selection button 122 for magnification to be displayed by operating the mouse etc., a bright field image and a fluorescence VS image which are displayed on the left side window 120 and the right side window 121 are simultaneously displayed in expanded size/reduced size, corresponding to this selected magnification. And, when a user, etc., operates the vertical and horizontal scroll button 123 with a mouse etc., the bright field image and the fluorescence VS image are displayed by scrolling simultaneously, and accordingly, a specimen with the same display magnification can be observed.

In the process mentioned above, deviation of the position of the specimen 19 accompanying mounting and demounting of the slide glass 40 is not taking into consideration. However, owing to the influence of mechanical precision etc., for example, there is a case that deviation of some XY-coordinates, and deviation of rotation may occur between the bright field image and the fluorescence VS image. A correction method is shown below. When a fluorescence indicator specimen is generated, besides a detection reagent, counter stain (nuclear dyeing as DAPI, etc.) is simultaneously carried out so that information locally contained in a cell of detection signal may be recognized. Accordingly, by deviation between a position of the nucleus on the bright field image and a position of the nucleus on the fluorescence VS image, the operator can recognize the position deviation between both images. Then, as shown in the left side window 120 in FIG. 9, when the operator etc., designates two or more nuclei so that these may be surrounded with a rectangle 125 (dotted line) on a bright field image, respectively (for example, these two tops which are faced are designated), these are displayed with the rectangle (dotted line) on the same coordinates in the same size also in the right side window 121 as illustrated. If there is no deviation of position/rotation between the bright field image and the fluorescence VS image, each nucleus displayed in the right side window 121 should be packed in each rectangle concerned, respectively. On the other hand, in the example illustrated, deviations are seen between each nucleus and the rectangle as shown.

In the present example, the operator can correct these deviations manually on the right side window 121. Namely, for example, by performing mouse operation (not illustrated) by the operator etc., each rectangle currently displayed in the right side window 121 can be moved toward XY directions (parallel translation), or moved by rotation, simultaneously. Thereby, the operator manually operates so as to move all the rectangles in the right side window 121 together by parallel translation, or by rotation movement, and adjusts so that each nucleus displayed in the right side window 121 may be packed in (surrounded by) each rectangle concerned, respectively. Thereby, the display in the right side window 121 becomes the state of right side window 121' shown by lower right portion in FIG. 9. Since deviation of position/rotation between the bright field image and the fluorescence VS image can be seen by detecting an amount of parallel displacement and an amount of rotation movement at this time, trimming (parallel translation correction) is carried out on the basis of the amount of the deviation of the parallel position to the fluorescence VS image currently displayed in the right side window 121, and rotation correction is carried out according to the amount of the deviation of the rotation. Thereby, its corrected image is generated. The corrected fluorescence VS image file generated in this way (not shown) is displayed in the right side window 121. The operator checks whether the process result is suitable or not, by seeing this displayed image. When it is suitable, the operator carries out a certain operation such as Check O.K. etc. By such operation, the corrected fluorescence VS image is overwritten on the existing fluorescence VS image. Thereby, the manual correction process mentioned above becomes unnecessary in the synchronous display from next time.

Figure 9:
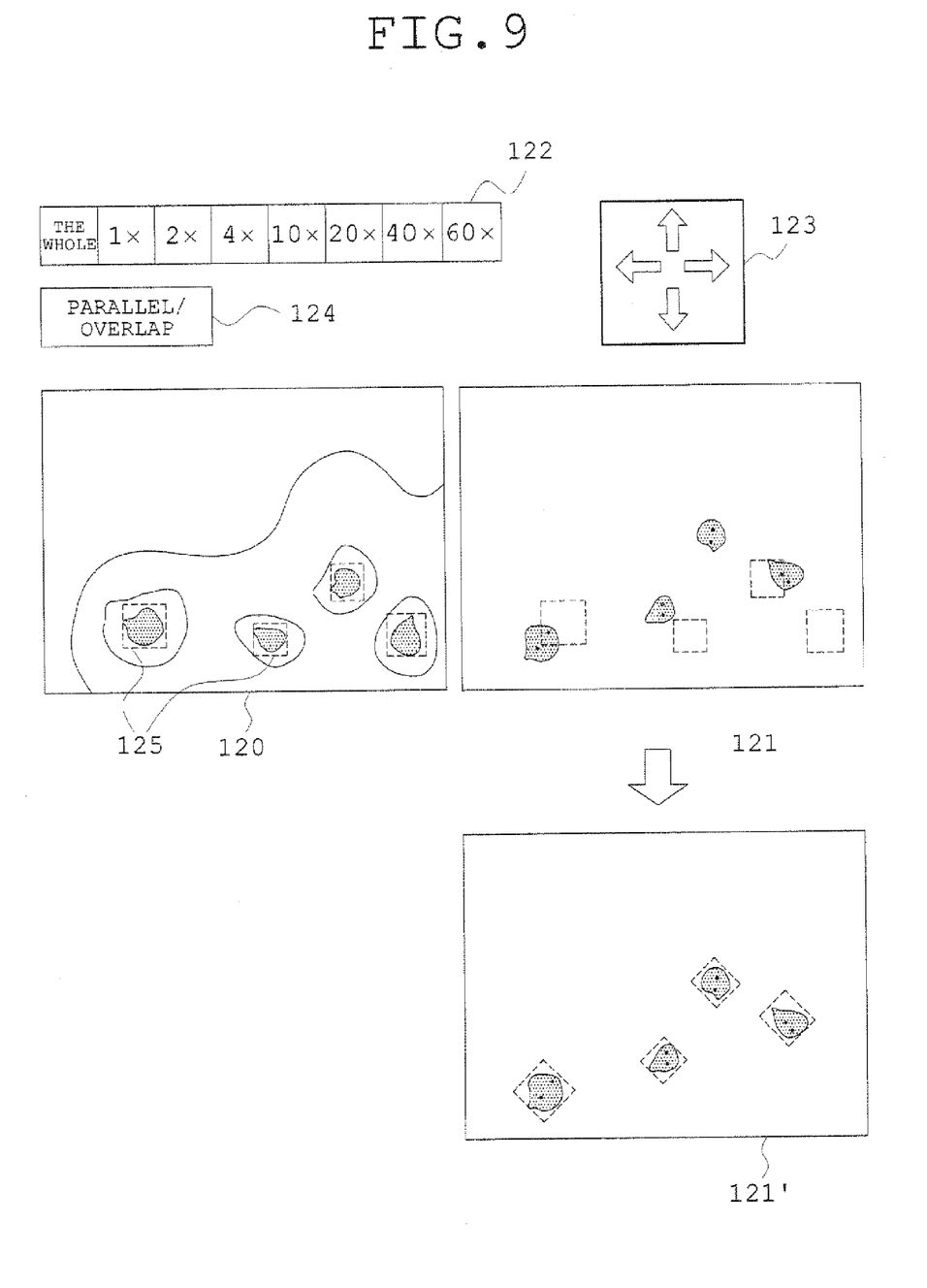
FIG. 9 is a diagram showing parallel/overlap display screen of VS images (two kinds) of an object of interest.

The example shown in FIG. 9 shows a case that the operator etc., operates "parallel/overlap" button 124 illustrated, and displays "parallel" is shown, and the bright field image and the fluorescence VS image are displayed side by side (parallel) as shown. However, when "overlap" indication is designated, only one window appears, two windows at right side and left side do not appear as two windows as mentioned above, but appears as one window only, and accordingly the bright field image and the fluorescence VS image will be displayed as overlapped images in this window (composite display). In this time, it is naturally possible that only the fluorescence signal portion (portion having a brightness more than a predetermined value) in the fluorescence VS image is displayed by overlapping with the bright field image, for example. Furthermore, it is also naturally possible that in the overlapped display mentioned above, the counter stain portion is used as a non-signal portion like a background portion. Naturally, it is also possible to constitute so as to blink a portion of the overlapped display. As a matter of course, it is possible to constitute such that a spatial relationship on a bright field image may be easily grasped, even in a state where images are not displayed as overlapped, by constituting that in a state that the images are displayed side by side (parallel), when a mouse cursor is placed, for example, in the left side window 120, a cursor is displayed also in the same window coordinates in the right side window 121.

As explained above, as for arbitrary objects of interest, two kinds of images (a bright field image and a fluorescence VS image) can be displayed side by side (parallel), or displayed as overlapped images, and a fluorescence VS image correlated with morphology information can be displayed. Since images as mentioned above can be observed, a morphological diagnosis and a molecular diagnosis can be confronted with each other, and accordingly, it can be contributed for achieving much more precise pathology diagnosis. Further, even when two kinds of images (a bright field image and a fluorescence VS image) about the object of interest are images which are not at the completely same portion (even in a case that each of the positions is deviated somehow), such deviation can be corrected easily by manual operation.

Next, the other embodiment according to the present invention will be explained.

In the embodiment mentioned above, deviation of the position of the specimen 19 accompanying mounting and demounting of the slide glass specimen is not taking into consideration, or since an amount of the deviation is very small, the process is premised that fine adjustment by manual operation mentioned above can be used. On the other hand, in the other embodiment described below, an example of process for meeting a case where deviation of position of the specimen 19 occurs by mounting and demounting the slide glass specimen will be shown. Namely, since HE dyeing and Papanicolaou dyeing for morphological observation, which were carried out to the specimen 19 in the case of process of FIG. 2, generates auto fluorescence signal, detection of gene/protein is hampered. Therefore, so far a process wherein the slide glass specimen which was dyed by Papanicolaou dyeing, etc., and is placed on the motorized stage 20 is once taken out, and a fluorescence sign is given after decoloring, and again, it is placed on the motorized stage 20 has been carried out. If a slide glass specimen is mounted or demounted manually as mentioned above, it is not always possible to return completely the specimen to the original position, and deviation of the position (parallel position gap) of XY coordinate may occur. That is, even if the XY coordinates of an arbitrary portion obtained before mounting and demounting are carried out is used the same portion cannot always be seen. Here, since a guide of the slide glass is usually placed on the motorized stage 20, it may be assumed that a rotation gap is not generated.

The other embodiment mentioned above corresponds to deviation of the position of the XY coordinate generated accompanying with mounting and demounting of the slide glass specimen (as mentioned above, it is assumed that a rotation gap does not occur, but only a parallel position gap occurs).

Figure 10:
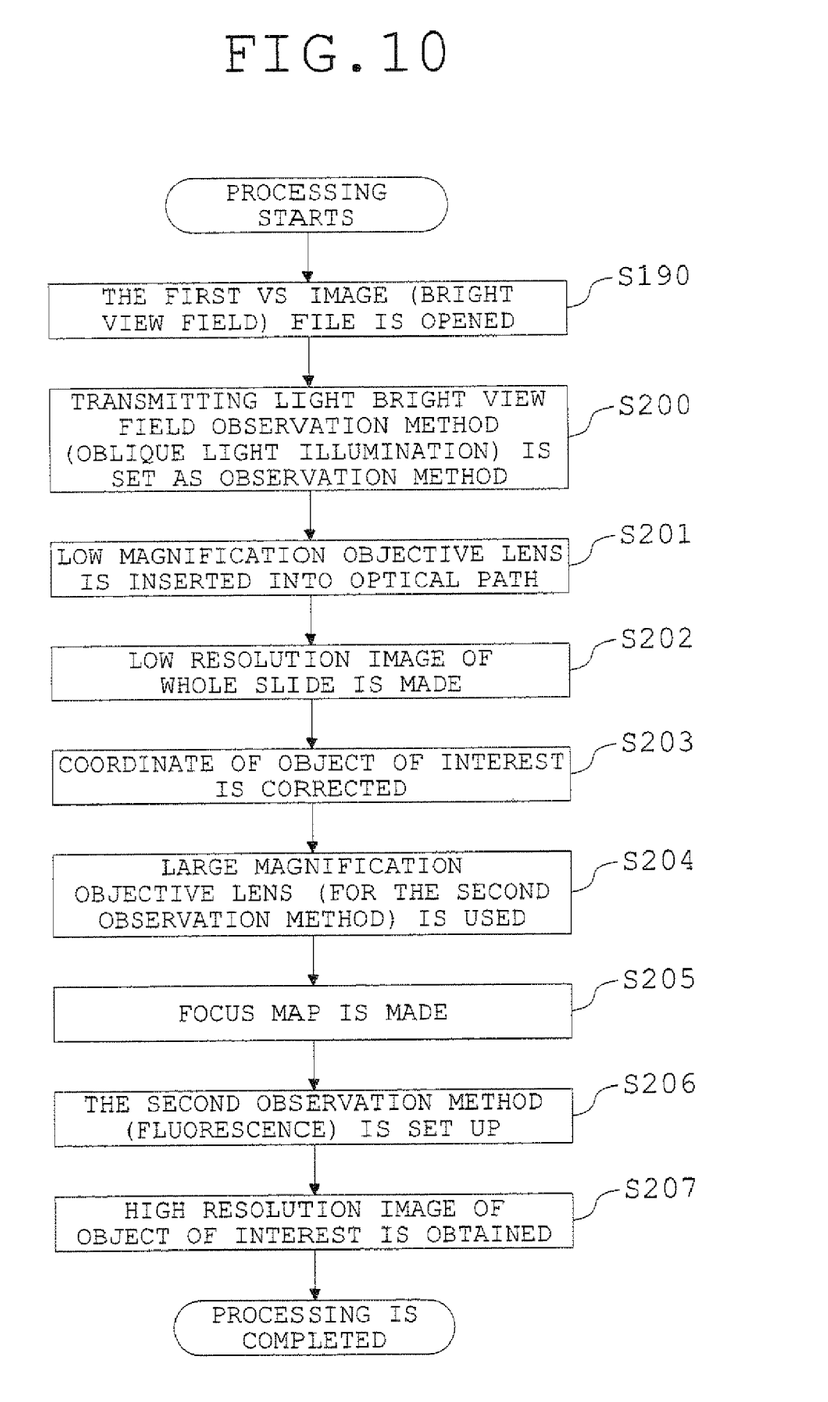
FIG. 10 is a flow chart showing a generating process of fluorescence VS-image of another embodiment.

FIG. 10 is a flow chart showing a process for generating of fluorescence VS-image of the other embodiment mentioned above. Here, the process shown in FIG. 10 is executed by the host system 2 as mentioned above. Namely, the process of FIG. 10 is realized by CPU, etc. (not illustrated) in the host system 2, wherein a predetermined application program stored in a memory storage (hard disk etc.) which is not illustrated, is read and executed. In the process of FIG. 10, the specimen 19 used in the process of FIG. 2 is used (however, decoloring→fluorescence sign was carried out to the specimen 19 before the process of FIG. 10 is carried out).

In FIG. 10, firstly, to a specimen before decoloring, namely, to a slide glass sample to which HE dyeing was carried out, a bright field VS image file generated and stored by the processes of the FIG. 2 etc., is opened (step 190). As for this process, for example, a slide sample number printed as a bar code on the label 43, etc., of the slide glass 40 is read by a barcode reader (not illustrated) connected to the host system 2, and the image file stored in the data recording part 4 is searched, and then a relevant bright view field VS image file can be selected automatically (naturally in this case, the slide sample number is contained in the title of image file).

Then, in the step S200, in order to realize slant-illumination by transmitting light bright view field observation method, control for inserting various optical components into an optical path and pulling them out is carried out. Namely, in order to set a transmitting light bright field observation state, by the host system 2a, the vertical light shutter 16 is inserted into an optical path via the microscope controller 31, and an optical cube 25 for bright field observation is inserted into the optical path, and a light source 6 for transmitting light illumination is lighted up, and furthermore, in order to realize slant light illumination, the transmitting light type aperture stop 10 is shifted by a predetermined distance from the optical axis. As for the reason for using slant light illumination, it is used because a specimen to which a fluorescence sign is given by decoloring is transparent in a non excitation state, and thus a position of the specimen cannot be checked by usual bright field observation. In that sense, it is not restricted to slant light illumination, phase difference observation method, and differentiation interferometer method can be used.

Next, in the step S201, objective lens 23 having low magnification such as four times is inserted into the optical path. Then, in the step S202, the nearly same process in the step S102 is carried out. Namely, by every each of portions that are formed by dividing a predetermined specimen search area 41

(for example, long: 25 mm×width: 50 mm) on the slide glass 40 shown in FIG. 3 according to a width of projection area which is to be projected on TV camera 3. A process for combining the inputted image with its adjoined image is carried out. That is, by moving the motorized stage 20 to XY directions, a microscopic image of blocks at the point where the stage was moved to, is repeatedly captured through TV camera 3. By combining mutually two or more micrographic images captured by the steps (images of each block by low magnification), a image (whole image with low magnification) of the whole specimen search area 41 is generated, and it is stored as a whole slide image file to the data recording section 4.

Then, in the step S203, an amount of deviated position of the specimen by mounting and demounting of the specimen is computed. On the basis of these values, coordinates of the object of interest to which fluorescence VS-image is generated (for example, the observation areas #1 and #2 etc.) are corrected. Namely, by comparing a specimen search area image data 62 in the bright view field VS image file opened at step S190 with an image of the whole specimen search area 41 generated by the step S202, the amount of deviation (the amount of parallel displacement) is computed. Concretely, by using a known image process algorithm, binary formatting is carried out to images of the two specimen search areas according to existence or non-existence of the specimen; and a profile of the specimen is extracted; and all the inside of the specimen (inside of the profile) is smeared as a specimen portion (data exists). Then, the center of gravity of each specimen area is obtained, and the difference of these two barycentric coordinates is obtained, and using this, the coordinate value of the object of interest is corrected. That is, upper left corner X coordinate 112 and upper left corner Y coordinate 113 in the object-of-interest designation information 64 of FIG. 6 are corrected. When there are two or more specimens as shown in FIG. 7, a center of gravity about one of arbitrary specimens may be obtained.

Since processes of subsequent steps S204-S207 are nearly same as those of step S151, and processes of S153-S155 mentioned above, the explanation is omitted. A fluorescence VS image is generated by these processes. The processes from steps S190 to S207 are automated, and by operator's action only for mounting the slide glass specimen 19 on the motorized stage 20, and carrying out a start operation for scanning of a scanning screen which is not illustrated, the fluorescence VS images of objects of interest (tumor site) are generated automatically. Therefore, if a conveying machine of the slide glass specimen is added to this system, a system by which the fluorescence VS images of the observation areas of two or more specimens 19 are automatically generated even in night time, etc., can be realized. Naturally, it is constituted so that correction may be made manually by an operator's intervention for stopping temporarily at each step of steps S190-S207 when an amount of position deviation of a specimen is larger than a value set arbitrarily beforehand for example. Furthermore, a predetermined marking is carried out to a non-specimen mount area on the object glass 40, and by calculating the amount of position deviation of the specimen based on this marking, correction of the coordinates of the object of interest can be generated.

As explained above, according to the present embodiment, even when the position of the specimen 19 is shifted by mounting and demounting of the object-glass specimen, the coordinate of the object of interest is corrected automatically. Accordingly, the fluorescence VS image of a designated object of interest (tumor part, etc.) is generated without problem. Furthermore, since two or more bright view field images, or fluorescence VS images of the specimen 19 can be generated automatically by combining with the slide glass specimen conveying apparatus etc., it contributes to labor saving.

Furthermore, other different embodiment will be described.

In a method in which HE dyeing and Papanicolaou dyeing are carried out to the specimen 19 for generating a bright view field VS image, and then decoloring and antigen activation process are carried out to this specimen 19 for generating fluorescence VS image, sometime it takes considerable time and effort, and also it may have a unfavorable influence on signal detection sensitivity. Therefore, in case of tissue specimen, a new specimen is sliced thinly from a paraffin embedding block, and fluorescence sign is given to this. In this case, since HE dyeing specimen and a fluorescence sign specimen are generated on separate slide glass 40 respectively, there is possibility that not only the parallel position deviation but also rotation deviation may occur. In the present embodiment, a method for generating a fluorescence VS image that copes with also such a case is proposed. The difference between process of the present embodiment and the process of FIG. 10 is only steps S203 and S207, and other processes are nearly the same. Therefore, explanation will be made without showing the flow chart of the present processes.

First, a process for correcting of coordinates of the object of interest in step S203 in the present embodiment is explained below. In this process, an amount of deviation (an amount of parallel displacement and rotation) is computed by comparing the specimen search area image data 62 in the bright view field VS image file opened at step S190 (hereafter, it is called as the whole specimen data A), and the whole image of the specimen search area 41 generated by the step S102 (hereafter, it is called as specimen data B). Concretely, for example, by using known image processing algorithms (correlation operation etc.), the two data mentioned above, namely, the whole specimen data A and the specimen data B are converted into binary format by which a specimen portion and a non specimen portion are distinguished respectively, and the profile of the specimen is extracted. Then, inside of the specimen (inside of the profile) is entirely smeared as a specimen portion where data exists (area of specimen portion is called specimen area). Then, the center of gravity of each specimen area is obtained, and the difference of these two barycentric coordinates is obtained. Next, in a state that the center of gravity of the specimen area of the whole specimen data B, and the center of gravity of the specimen area of the whole specimen data A are coincided, for example, the specimen area of the whole specimen data B is rotated in clockwise direction by a predetermined angle unit (example: 0.1 degree) around the center of gravity and an angle (amount of rotation) at which absolute value of difference between the whole specimen data B and the specimen area of the whole specimen data A becomes minimum is obtained.

The difference of the barycentric coordinates, and the amount of rotation (rotation direction is also included) which were obtained as mentioned above, expresses a relation of the deviation of position of the specimen on the motorized stage 20. And, by carrying out affine transformation (parallel translation and rotation movement) of the coordinates of the object of interest currently recorded into the bright view field VS image file by using the difference of the barycentric coordinates, and the amount of rotation which were obtained, the coordinate value of an object of interest is corrected, and then the coordinate value corrected is recorded by overwriting. In the process of step S207 in the present embodiment, after the process for generating the fluorescence VS image mentioned above, furthermore, the following processes are added.

Namely, the generated fluorescence VS image has become an image in which the specimen has been rotated by the amount of rotation obtained in the step S203 when it is compared with the bright field image of the same object of interest. Therefore, by rotating the generated fluorescence VS image toward an opposite direction against the rotation direction obtained at step S203 according to the amount of the rotation, generating of a fluorescence VS image is completed, and this is recorded as a fluorescence VS image file. When the amount of deviation obtained at step S203 is larger than a predetermined value, as a matter of course, it can be corrected manually.

According to the present embodiments as explained above, even if the deviation of the coordinates of XYθ including rotation owing to the difference of mounting of the specimen on the slide glass occurs, the fluorescence VS image of a desired tumor part can be generated.

As explained above, the deviation of position of the specimen, which is caused by using a method, wherein a normal dyeing specimen used in a bright field observation method is decolorized, and a fluorescence sign is given, or using a method, wherein a fluorescence sign is given to series of sliced piece, for generating a VS image in a fluorescence observation method after a specimen image is generated in the bright view field observation method is detected, and then the object of interest coordinate is corrected.

Thereby, the fluorescence VS image of the observation area mentioned above can be generated correctly.

What is claimed is:

1. In a microscope system including
   an optical system constructed and arranged to form a microscopic image of a specimen under a selected one of a plurality of microscopy modes that include a bright-field observation mode and a fluorescence observation mode, and
   a stage for holding the specimen, configured to be movable relative to the optical system,
   an image pickup unit for picking up the microscopic image formed by the optical system of the microscope, and
   a host system for controlling the microscope system, a method performed by the host system for virtual slide (VS) image generation comprising the steps of:
      forming a plurality of bright-field images corresponding to a first plurality of divisions of an area of the specimen, under the bright-field observation mode upon moving the stage, on which the specimen is held, relative to the optical system of the microscope, and combining together, by arraying, the plurality of bright-field images as picked up by the image pickup unit into a bright-field VS image of the specimen area;
      displaying the bright-field VS image of the specimen area on a monitor to be viewed by the user and receiving user selections of one or more objects of interest of the bright-field VS image using an input section of said host system;
      forming a plurality of fluorescence images corresponding to a second plurality of divisions, into which each of the selected one or more objects of interest is divided, under the fluorescence observation mode upon moving the stage relative to the optical system of the microscope, and combining together, by arraying, the plurality of fluorescence images as picked up by the image pickup unit into a fluorescence VS image of each of the selected one or more objects of interest;
      receiving a user choice among the objects of interest, and displaying, side by side on the monitor, a chosen object of interest clipped out from the bright-field VS image of the specimen area and a fluorescence VS image of the selected object of interest;
      receiving user settings for a plurality of boxes to enclose a plurality of cell nuclei, respectively, on the bright-field VS image of the selected object of interest, and displaying a plurality of boxes at corresponding coordinates in the fluorescence VS image of the selected object of interest;
      receiving user adjustments to positions of the plurality of boxes on the fluorescence VS image of the selected object of interest by parallel-shifting and rotating the plurality of boxes collectively until a plurality of cell nuclei appearing in the fluorescence VS image of the selected object of interest are enclosed in the plurality of boxes;
      determining values of deviation with respect to parallel position and with respect to rotation between the bright-field VS image of the selected object of interest and the fluorescence VS image of the selected object of interest, from positions of the plurality of boxes on the bright-field VS image of the selected object of interest and positions of the plurality of boxes on the fluorescence VS image of the selected object of interest after being adjusted by the user;
      performing parallel-shift correction and rotation correction on a basis of the values of deviation with respect to parallel-position and with respect to rotation, to generate a corrected fluorescence VS image; and
      displaying the corrected fluorescence VS image.

* * * * *